United States Patent [19]

Wolfers et al.

[11] 4,163,865
[45] Aug. 7, 1979

[54] PROCESS FOR THE PREPARATION OF PINACOLS

[75] Inventors: Heinrich Wolfers, Rheurdt; Hans Rudolph; Hans-Jurgen Rosenkranz, both of Krefeld, all of Fed. Rep. of Germany

[73] Assignee: Bayer Aktiengesellschaft, Leverkusen, Fed. Rep. of Germany

[21] Appl. No.: 893,097

[22] Filed: Apr. 3, 1978

[30] Foreign Application Priority Data

Apr. 22, 1977 [DE] Fed. Rep. of Germany ....... 2718104

[51] Int. Cl.$^2$ ............................................. C07C 29/00
[52] U.S. Cl. ................................ 568/640; 260/308 R; 260/563 R; 260/563 P; 260/570 AB; 260/570.5 R; 260/570.5 P; 260/570.5 CA; 260/570.5 S; 260/570.6; 260/570.7; 260/571; 260/573; 260/575; 260/576; 260/577; 260/578; 260/583 E; 260/583 EE; 260/583 GG; 260/583 P; 260/584 R; 260/584 C; 260/609 E; 260/609 F; 568/630; 568/631; 568/632; 568/633; 568/634; 568/641; 568/643; 568/644; 568/645; 568/648; 568/649; 568/655; 568/656; 568/658; 568/660; 568/661; 568/662; 568/663; 568/664; 568/669; 568/670; 568/677; 568/676; 568/678; 568/679; 568/680; 568/715; 568/807; 568/811; 568/816; 568/821; 568/827; 568/838; 568/842; 568/846; 568/862

[58] Field of Search ............... 568/630, 631, 632, 633, 568/634, 641, 643, 644, 645, 648, 649, 655, 656, 658, 660, 661, 662, 663, 664, 669, 670, 672, 676, 677, 678, 679, 680, 715, 807, 811, 816, 821, 822, 838, 842, 846, 862, 640; 260/308 R, 609 E, 609 F, 563 R, 563 P, 570 AB, 570.5 R, 570.5 P, 570.5 CA, 570.5 S, 570.6, 570.7, 571, 573, 575, 576, 577, 578, 583 EE, 583 G, 583 GG, 583 P, 584 R, 584 C

[56] References Cited

U.S. PATENT DOCUMENTS 1,752,016   3/1930   Maximoff ............................ 568/862

FOREIGN PATENT DOCUMENTS 511462   3/1955   Canada ..................................... 568/811
890643   8/1953   Fed. Rep. of Germany ........... 568/862
49-27079 9/1975  Japan ...................................... 568/811
3690     5/1919   Netherlands ............................. 568/862
44222    3/1961   Poland ..................................... 568/811
54686    4/1911   Switzerland ............................. 568/862
55670    4/1911   Switzerland ............................. 568/862
56841    8/1911   Switzerland ............................. 568/862
642752   9/1950   United Kingdom ..................... 568/862

OTHER PUBLICATIONS

Houben-Wexl, "Methoden der Organische Chemie", vol. 7/26, 4th Ed., p. 2002 (1976).
"Organic Synthesis", vol 14, p. 9 (1934).
"J.A.C.S.", vol. 49, p. 241 (1925).
"J.A.C.S.", vol. 55, p. 1181 (1933).
Oxama, "J. Org. Chem., vol. 1965, pp. 2429-2432.
"Chem. Reviews," vol. 57, p. 424.

*Primary Examiner*—Norman Morgenstern
*Attorney, Agent, or Firm*—Sprung, Felfe, Horn, Lynch & Kramer

[57] ABSTRACT

An improvement in a process for the preparation of a pinacol of the formula

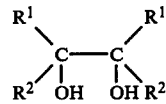

wherein
$R^1$ and $R^2$ are identical or different and represent optionally substituted aliphatic, cycloaliphatic, araliphatic or an aromatic hydrocarbon radical by reducing a ketone of the formula

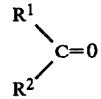

wherein
$R^1$ and $R^2$ have the abovementioned meanings with a base metal, the improvement comprising carrying out the reduction in the presence of an organic halogen compound and in the presence of a phosphoric acid amide, phosphoric acid ester and/or carboxylic acid amide.

15 Claims, No Drawings

PROCESS FOR THE PREPARATION OF PINACOLS

The invention relates to a process for the preparation of pinacols by reducing ketones with base metals.

It is known to prepare pinacols by the action of reactive metals on ketones or by the electrolytic reduction of ketones (compare, for example, Houben-Weyl, Methoden der organischen Chemie (Methods of Organic Chemistry), volume 7/2b, 4th edition, page 2,002 (1976)).

Furthermore, it is known to prepare benzopinacol by the photochemical reduction of benzophenone in isopropanol (Organ. Synthesis, volume 14, page 9 (1934)).

However, it is common to the abovementioned processes that when they are converted to an industrial scale the expenditure on apparatus becomes very high, whereby the profitability suffers.

Furthermore, it is known from the literature (J. Amer. Chem. Soc. 49, 241 (1927) and 55, 1,181 (1933) as well as Chem. Rev. 57, 424) to convert aromatic ketones, for example benzophenones, in ether or mixtures of ether and aromatic solvents in the presence of magnesium and magnesium bromide or magnesium iodide into pinacols.

Large amounts of anhydrous organic solvents, such as ether and aromatic solvents, as well as anhydrous reducing agents, such as magnesium and magnesium bromide or magnesium iodide, are required for this process.

When carried out on an industrial scale, this procedure is not only associated with high costs, but also pollutes the effluent to a considerable extent.

A process has now been found for the preparation of pinacols of the general formula

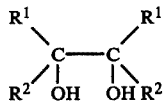 (I)

wherein $R^1$ and $R^2$ are identical or different and represent an optionally substituted aliphatic, cycloaliphatic, araliphatic or aromatic hydrocarbon radical, by reducing ketones of the general formula

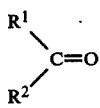 (II)

wherein $R^1$ and $R^2$ have the abovementioned meaning, with base metals, which is characterised in that the reduction is carried out in the presence of organic halogen compounds and in the presence of phosphoric acid amides, phosphoric acid esters and/or carboxylic acid amides.

Examples which may be mentioned of optionally substituted aliphatic hydrocarbon radicals $R^1$ and $R_2$ are straightchain or branched aliphatic hydrocarbon radicals with up to 12, preferably with up to 6, carbon atoms. The following hydrocarbon radicals, for example, are possible: methyl, ethyl, n-propyl, iso-propyl, n-butyl, iso-butyl, tert.-butyl, n-pentyl, neopentyl, n-hexyl, iso-hexyl and trifluoromethyl.

Examples of possible optionally substituted cycloaliphatic radicals $R^1$ and $R^2$ are those with 5 to 12, preferably 5 to 6, carbon atoms, such as the cyclopentyl, the cyclohexyl or methylcyclohexyl, the cycloheptyl, the cyclooctyl and the cyclododecyl radical, preferably the cyclopentyl and cyclohexyl radical.

Examples of possible optionally substituted araliphatic radicals $R^1$ and $R^2$ are those with 7 to 18 carbon atoms, the aliphatic part of which contains 1 to 6 carbon atoms and the aromatic part of which is a radical of the benzene series. Examples which may be mentioned are the following araliphatic radicals: the β-ethyl-phenyl, the γ-propyl-phenyl, the β-phenyl-n-hexyl, the β-[naphthyl-(1)]-ethyl, the ω-butylphenyl, the ω-pentylphenyl and the ω-hexyl-phenyl radical.

Optionally substituted aromatic radicals $R^1$ and $R_2$ can be the phenyl, the naphthyl, the phenanthryl, the tetrazyl, the anthracyl and the diphenyl radical, preferably the phenyl and the naphthyl radical.

Possible substituents of the aliphatic, cycloaliphatic, araliphatic and aromatic hydrocarbon radicals are substituents which are not altered under the reaction conditions. Examples which may be mentioned are: the halogens, such as fluorine and chlorine, the amino group, which can be monosubstituted or disubstituted by alkyl or aryl radicals with up to 12, preferably up to 6, C atoms, such as the methylamino, the dimethylamino, the phenylamino and the diethylamino group; straight-chain or branched alkyl radicals with up to 6 carbon atoms, such as the methyl, ethyl, propyl, isopropyl, tert.-butyl, pentyl and hexyl radical; aryl radicals, such as the phenyl and the naphthyl radical; the alkoxy group with up to 6 carbon atoms, such as the methoxy, ethoxy, propoxy and butoxy group; and the alkylmercapto group with up to 6 carbon atoms, such as the methylmercapto and the ethylmercapto group.

The ketones of the formula (II) which are used for the process according to the invention are known. Examples which may be mentioned are: acetophenone, 2-chloracetophenone, propiophenone, isopropyl phenyl ketone, 4-chloroisopropyl phenyl ketone, tert.-butyl phenyl ketone, 3-fluoro-tert.-butyl phenyl ketone, cyclopentyl phenyl ketone, cyclohexyl phenyl ketone, benzophenone, 2-chlorobenzophenone, 3-fluorobenzophenone, 4-chlorobenzophenone, 3-methoxybenzophenone, 4-phenylbenzophenone, 2,4'-dichlorobenzophenone, 4,4'-diethylbenzophenone, 4,4'-bis-(dimethylamino)-benzophenone, 2-methylbenzophenone, 2,4-dimethylbenzophenone, 2,4,2',4'-tetrachlorobenzophenone and ω-trifluoroacetophenone.

Acetophenone, pripiophenone, isopropyl phenyl ketone, tert.-butyl phenyl ketone, cyclohexyl phenyl ketone, benzophenone, 4,4'-dimethylbenzophenone, 4-chlorobenzophenone, 3-methoxybenzophenone, 4-phenykbenzophenone, 2,4'-dichlorobenzophenone, 4,4'-dichlorobenzophenone, 2-methylbenzophone and 2,4,2', 4'-tetrachlorobenzophenone are preferred.

The base metals suitable for reducing the ketones are in themselves known. Examples which may be mentioned are: the metals of main groups 1 and 2 of the Periodic System, such as lithium, sodium, potassium, beryllium, magnesium and calcium, as well as metals of main group 3 of the Periodic System, such as aluminium.

The following metals are preferably used for the process according to the invention: sodium, magnesium and aluminium.

Examples of possible organic halogen compounds are straight-chain or branched alkyl halides with up to 18, preferably up to 12, carbon atoms, such as methyl iodide, n-butyl chloride, tert.-butyl chloride, pentyl chloride, hexyl chloride, methylene chloride, dichloroethane, chloroform, carbon tetrachloride, tetrachloroethane, hexachloroethane, isopropyl bromide, bromoform and iodoform, and furthermore cycloalkyl halides with up to 12 carbon atoms, preferably up to 7 carbon atoms, such as cyclopentyl chloride, cyclohexyl chloride, cycloheptyl chloride, methylcyclohexyl chloride, cyclohexyl bromide and cyclohexyl iodide; araliphatic halogen compounds with up to 18 carbon atoms, preferably up to 12 carbon atoms, such as benzyl chloride, benzal chloride, benzotrichloride, benzyl bromide, $\beta$-phenylethyl chloride, xylidene dichloride, xylidene dibromide and benzyl iodide; aromatic halogen compounds with up to 14 carbon atoms, preferably up to 10 carbon atoms, such as bromobenzene, chlorobenzene, dichlorobenzene, p-chlorodiphenyl, chloronaphthalene, dibromophenanthrene and iodobenzene, as well as halides of aliphatic or aromatic carboxylic acids with up to 12 carbon atoms, preferably up to 7 carbon atoms, such as acetyl chloride, propionyl chloride, benzoyl chloride, chloroformic acid ethyl ester and phosgene.

Methylene chloride, chloroform, isopropyl bromide, dichloroethane, bromobenzene, benzyl chloride and methyl iodide are preferably used in the process according to the invention.

The organic halogen compounds can be employed by themselves or mixed with one another.

The process according to the invention is carried out in the presence of phosphoric acid amides, phosphoric acid esters and/or carboxylic acid amides, with the addition of inert organic solvents.

Suitable phosphoric acid amides are the N,N-disubstituted triamides, such as hexamethylphosphoric acid triamide, hexaethylphosphoric acid triamide and hexabutylphosphoric acid triamide. Hexamethylphosphoric acid triamide and hexaethylphosphoric acid triamide are preferably employed. $C_1$–$C_8$ phosphoric acid alkyl amides are particularly contemplated.

Phosphoric acid esters which can be used are the triesters with up to 6 carbon atoms, especially the alkyl esters. In these esters, the ester groups can be identical or different. Examples of ester groups which may be mentioned are: the methyl, ethyl, isopropyl, butyl, hexyl and phenyl ester group.

Triethyl phosphate, tributyl phosphate and triisopropyl phosphate are preferably employed.

Carboxylic acid amides which can be used are the N,N-disubstituted amides of aliphatic carboxylic acids with up to 8, and preferably up to 6, carbon atoms, it being possible for the amide substituents to be identical or different. Particularly contemplated are the $C_1$–$C_6$ alkyl amides.

Examples which may be mentioned are: N,N-dimethylformamide, N,N-dimethylacetamide, N,N-diethylformamide, N,N-diethylpropionamide and N-methylpyrrolidone.

N,N-Dimethylformamide and N,N-dimethylacetamide are preferably employed.

Organic solvents which can be used are all the solvents which are inert under the reaction conditions. Examples which may be mentioned are: aliphatic hydrocarbons with up to 14, preferably up to 10, carbon atoms, such as pentane, iso-pentane, hexane, iso-hexane, heptane, iso-heptane, n-octane, iso-octane and n-decane; cycloaliphatic hydrocarbons with up to 12, preferably up to 10, carbon atoms, such as cyclopentane, cyclohexane, methylcyclohexane, cycloheptane and decalin; aromatic hydrocarbons with up to 14, preferably with up to 10, carbon atoms, such as benzene, toluene, xylene, mesitylene, anisole, tetralin and ethylbenzene; and aliphatic and cycloaliphatic ethers with up to 16, preferably up to 10, carbon atoms, such as diethyl ether, diisopropyl ether, dibutyl ether, tetrahydrofurane and dioxane.

Tetrahydrofurane, dioxane, diethyl ether and anisole are preferably employed in the process according to the invention.

In general, the amount of solvents added, which can be employed alone or mixed with one another, is about 1 to 15 parts by weight, preferably 1 to 3 parts by weight, relative to 1 part by weight of ketone.

In general, molar ratios of ketone to base metal of about 1:0.33 to 1:2 are used for carrying out the process according to the invention. A molar ratio of ketone to base metal of 1:0.34 to 1:1.2 is preferred.

The organic halogen compounds are employed in approximately catalytic amounts, relative to the ketones employed. In general, the process according to the invention is carried out in the presence of about 0.01 to 20 mol%, preferably 0.02 to 5 mol%, relative to the ketone employed. However, even amounts which are smaller than 0.01 mol% are sufficient for carrying out the process.

The amount of phosphoric acid amides, phosphoric acid esters and/or carboxylic acid amides employed is not critical. It can be chosen so that after working up the reaction mixture a solution of the pinacol in the acid amides or esters is obtained. In general, the amides or esters are added in amounts of about 2 to 400 parts by weight, preferably 5 to 150 parts by weight, relative to 100 parts by weight of ketone employed.

The process according to the invention can be carried out at temperatures in a range from about $-5$ to $110°$ C., preferably at 10 to 80° C.

In general, the reaction is carried out as follows: the ketone, together with the organic halogen compound and an inert organic solvent, is added to a suspension of the base metal in a solution of phosphoric acid amides, phosphoric acid esters and/or carboxylic acid amides and an inert organic solvent, whilst stirring. The mixture is stirred at the reaction temperature until all the metal has been consumed. Thereafter, the reaction mixture is hydrolysed with water, glacial acetic acid or a solution of an organic or inorganic acid, diluted with water; the organic phase is separated off, washed, dried and concentrated. The pinacol or a solution of the pinacol in an organic solvent remains.

Since the reaction generally proceeds strongly exothermically, it is advisable to cool the reaction mixture. In certain circumstances it is possible that partial decomposition of the pinacols occurs under the reaction conditions, especially if relatively high temperatures are used. Thus, if the yield of the corresponding pinacol is too low, the reaction temperature should be lowered and, if appropriate, the base metal should be activated by small amounts, about 0.01 to 0.1 part by weight (relative to the base metal), of a mercury salt, such as $Hg_2Cl_2$, $HgCl_2$ or $Hg(NO_3)_3$.

The process according to the invention has the following advantages: it is a process which is economic and can be easily carried out industrially. It proceeds without large amounts of solvents. The base metals can be employed directly as the reducing agent, good yields of pinacols being obtained.

The process according to the invention is illustrated with the aid of the following examples, but without being limited to these examples.

EXAMPLE 1

25 g of ground Mg filings are covered with 100 ml of tetrahydrofurane and 150 ml of hexamethylphosphoric acid triamide in a 2 l three-necked flask. A solution of 364 g of benzophenone in 10 g of methylene chloride, 200 ccs of tetrahydrofurane and 400 ccs of toluene is added dropwise at 30 to 40° C., whilst stirring vigorously. During this period, the reaction solution is flushed with dried nitrogen.

The start of the reaction can be detected by an intensive blue colouration. When the dropwise addition of the benzophenone solution is complete, the mixture is further stirred at 30 to 40° C. until the magnesium has completely dissolved. The mixture is then hydrolysed with one litre of dimolar HCl and the organic phase is separated off and washed several times with water. After stripping off the solvent, the residue is recrystalised from isopropanol. Yield: 90% of theory.

EXAMPLE 2

24.5 of ground Mg filings are covered with 100 ml of tetrahydrofurane in a 2 l three-necked flask. A solution of 364 g of benzophenone, 10 ml of ispropyl bromide and 500 ml of triethyl phosphate in 800 ml of toluene is then added dropwise at a bath temperature of 40° C. When the magnesium filings have dissolved and the exothermic reaction has subsided, the mixture is stirred for a further 1 hour. For the hydrolysis, first 120 g of glacial acetic acid and then 800 ml of water are added dropwise.

The organic phase is separated off, washed three times with water and concentrated in a Rotavapor at 40° C. A solution, which can be readily pumped, of benzopinacol in triethyl phosphate remains as the residue. The pinacol is precipitated quantitatively on diluting the solution with methanol and water. Yield 95% of theory.

Instead of the isopropyl bromide, it is also possible to use, for example, benzyl chloride, benzal chloride, methyl iodide or methylene chloride.

EXAMPLE 3

Example 2 is repeated, but 240 g of acetophenone are employed instead of the benzophenone. Furthermore, 0.05 g of $HgCl_2$ are added to increase the activity of the magnesium.

After the working up, a solution of the pinacol in triethyl phosphate remains.

Yield: 75% of theory.

EXAMPLE 4

Example 1 is repeated, but 20 g of aluminium are employed instead of the magnesium. 0.05 g of $HgCl_2$ are added to increase the activity of the aluminium.

The product which remains after the working up contains benzopinacol to the extent of about 85 to 90% of theory (relative to benzophenone employed).

EXAMPLE 5

Example 2 is repeated, but 296 g of isopropyl phenyl ketone are employed instead of the benzophenone. 0.05 g of $HgCl_2$ are added to increase the activity of the magnesium. Yield: 85% of theory.

EXAMPLE 6

3 g of Mg filings and a pinch of $HgCl_2$ are covered with 300 ml of dried tetrahydrofurane and 100 ml of distilled dimethylformamide in a 500 ml three-necked flask. 60 g of 4-chlorobenzophenone and 3×2 drops of bromobenzene are added, in several portions, to this suspension, whilst stirring. In the course of 4 hours, the Mg dissolves and the solution becomes green-black in colour. For working up, the solution is added to 50 ml of glacial acetic acid, the mixture is diluted with toluene and water and the organic phase is separated off. After washing the organic phase several times with water, the toluene is stripped off. A solid remains, from which 40 g of 1,2-diphenyl-1,2-bis-(4-chlorophenyl)-ethanediol (66% of theory) could be isolated by recrystallisation from isopropanol/benzene.

EXAMPLE 7

Example 6 was repeated, but 54 g of 4-methylbenzophenone were employed instead of the 4-chlorobenzophene and benzoyl chloride was employed instead of the bromobenzene. The solid which remains after the working up was also recrystallised from isopropanol/benzene. The yield was 58% of theory.

What is claimed is:

1. An improvement in a process for the preparation of a pinacol of the formula

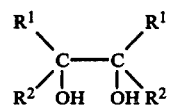

wherein
$R^1$ and $R^2$ are identical or different and represent optionally substituted aliphatic, cycloaliphatic, araliphatic or an aromatic hydrocarbon radical
by reducing a ketone of the formula

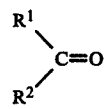

wherein
$R^1$ and $R^2$ have the abovementioned meanings with a base metal, the improvement comprising carrying out the reduction in the presence of an organic halogen compound and in the presence of a phosphoric acid amide, phosphoric acid ester and/or carboxylic acid amide.

2. Process according to claim 1 wherein the ketone is acetophenone, propiophenone, isopropyl phenyl ketone, t-butyl phenyl ketone, cyclohexyl phenyl ketone, benzophenone, 4,4-dimethylbenzophenone, 4-chlorobenzophenone, 3-methoxybenzophenone, 4-phenylbenzophenone, 2,4′-dichlorobenzophenone, 4,4′-dichlorobenzophenone, 2-methylbenzophenone or 2,4,2′,4′-tetrachlorobenzophenone.

3. A process according to claim 1 wherein the reaction is carried out at a temperature in the range of −5 to +110° C.

4. A process according to claim 1 wherein the reaction is carried out in the presence of 0.01 to 20 mol percent of organic halogen compound relative to the amount of ketone employed.

5. A process according to claim 1 wherein the reaction is carried out in the presence of 2 to 400 parts by weight of phosphoric acid amide, phosphoric acid ester and/or carboxylic acid amide, relative to 100 parts by weight of ketone.

6. A process according to claim 1 wherein the molar ratio of ketone to base metal is 1:0.33-2.

7. A process according to claim 1 wherein the organic halogen compound is an alkyl halide having up to 18 carbon atoms, a cycloalkyl halide having up to 12 carbon atoms, an araliphatic halogen compound having up to 18 carbon atoms or an aromatic halogen compound having up to 14 carbon atoms.

8. A process according to claim 1 wherein the reaction is carried out in the presence of a phosphoric acid amide.

9. A process according to claim 8 wherein said phosphoric acid amide is hexamethylphosphoric acid triamide, hexaethylphosphoric acid triamide or hexabutylphosphoric acid triamide.

10. A process according to claim 1 wherein the process is carried out in the presence of a phosphoric acid ester and said phosphoric acid ester has up to 6 carbon atoms in each of the ester groups.

11. A process according to claim 10 wherein said phosphoric acid ester is a trialkyl ester of phosphoric acid and the alkyl group is methyl, ethyl, isopropyl, butyl or hexyl.

12. A process according to claim 1 wherein the reaction is carried out in the presence of a phosphoric acid phenyl ester.

13. A process according to claim 1 wherein the reaction is carried out in the presence of a carboxylic acid amide.

14. A process according to claim 13 wherein said carboxylic acid amide is a N,N-disubstituted amide of an aliphatic carboxylic acid having up to 8 carbon atoms.

15. A process according to claim 14 wherein said carboxylic acid amide is N,N-dimethylformamide, N,N-dimethylacetamide, N,N-diethylformamide, N,N-diethypropionamide or N-methylpyrrolidone.

* * * * *